US011071648B2

(12) United States Patent
Muehlhoff et al.

(10) Patent No.: US 11,071,648 B2
(45) Date of Patent: *Jul. 27, 2021

(54) METHOD AND DEVICE FOR PRODUCING CURVED CUTS IN A TRANSPARENT MATERIAL

(71) Applicant: Carl Zeiss Meditec AG, Jena (DE)

(72) Inventors: Dirk Muehlhoff, Jena (DE); Mario Gerlach, Glienicke-Nordbahn (DE); Markus Sticker, Jena (DE); Carsten Lang, Eisenberg (DE); Mark Bischoff, Jena (DE); Michael Bergt, Weimar (DE)

(73) Assignee: Carl Zeiss Meditec AG, Jena (DE)

( * ) Notice: Subject to any disclaimer, the term of this patent is extended or adjusted under 35 U.S.C. 154(b) by 132 days.

This patent is subject to a terminal disclaimer.

(21) Appl. No.: 16/274,925

(22) Filed: Feb. 13, 2019

(65) Prior Publication Data

US 2019/0247226 A1    Aug. 15, 2019

Related U.S. Application Data

(63) Continuation of application No. 10/566,009, filed as application No. PCT/EP2004/008279 on Jul. 23, 2004, now Pat. No. 10,213,339.

(30) Foreign Application Priority Data

Jul. 25, 2003 (DE) ................................ 103 34 110.2

(51) Int. Cl.
*A61F 9/008*    (2006.01)
*A61F 9/009*    (2006.01)

(52) U.S. Cl.
CPC .......... *A61F 9/008* (2013.01); *A61F 9/00829* (2013.01); *A61F 9/009* (2013.01);
(Continued)

(58) Field of Classification Search
CPC ................................ A61F 9/008; A61F 9/009
See application file for complete search history.

(56) References Cited

U.S. PATENT DOCUMENTS

| 4,721,379 A | 1/1988 | L'Esperance |
| 4,901,718 A | 2/1990 | Bille et al. |

(Continued)

FOREIGN PATENT DOCUMENTS

| DE | 101 24 358 C1 | 10/2002 |
| DE | 103 23 422 A1 | 4/2004 |

(Continued)

OTHER PUBLICATIONS

Application and File History for U.S. Appl. No. 10/566,009, filed Jan. 25, 2006. Inventors: Dirk Muehlhoff et al.

*Primary Examiner* — Lynsey C Eiseman

(74) *Attorney, Agent, or Firm* — Patterson Thuente Pedersen, P.A.

(57) ABSTRACT

The invention relates to a method for forming curved cuts in a transparent material, in particular in the cornea, by the creation of optical perforations in said material using laser radiation that is focused in the material. The focal point is displaced three-dimensionally to form the cut by lining up the optical perforations. The focal point is displaced in a first spatial direction by a displaceable lens and said focal directions, in such a way that it follows the contours of the cut, which lie on a plane that is substantially perpendicular to the first spatial direction.

26 Claims, 4 Drawing Sheets

(52) U.S. Cl.
CPC .............. *A61F 2009/00872* (2013.01); *A61F 2009/00897* (2013.01)

(56) References Cited

U.S. PATENT DOCUMENTS

| | | |
|---|---|---|
| 5,549,632 A | 8/1996 | Lai |
| 5,928,221 A | 7/1999 | Sasnett et al. |
| 5,984,916 A | 11/1999 | Lai |
| 5,993,438 A | 11/1999 | Juhasz et al. |
| 6,110,166 A | 8/2000 | Juhasz |
| 6,325,792 B1 | 12/2001 | Swinger et al. |
| 6,338,559 B1 | 1/2002 | Williams et al. |
| 6,497,701 B2 | 12/2002 | Shimmick et al. |
| 6,608,674 B2 | 8/2003 | Gerlach et al. |
| 6,805,694 B2 | 10/2004 | Donitzky |
| 7,101,364 B2 | 9/2006 | Bille |
| 2001/0031960 A1 | 10/2001 | Kliewer et al. |
| 2002/0103481 A1* | 8/2002 | Webb ..................... A61F 9/009 606/5 |
| 2003/0014042 A1 | 1/2003 | Juhasz et al. |
| 2003/0105457 A1 | 6/2003 | Mrochen et al. |
| 2004/0243112 A1* | 12/2004 | Bendett ................. A61F 9/0084 606/5 |
| 2005/0107773 A1 | 5/2005 | Bergt et al. |

FOREIGN PATENT DOCUMENTS

| | | |
|---|---|---|
| WO | WO 93/16631 | 9/1993 |
| WO | WO 94/09849 | 5/1994 |
| WO | WO 97/30752 | 8/1997 |
| WO | WO 98/14244 | 4/1998 |
| WO | WO 01/67978 A1 | 9/2001 |
| WO | WO 01/85075 A1 | 11/2001 |
| WO | WO 02/32353 A2 | 4/2002 |
| WO | WO 03/059563 A2 | 7/2003 |

\* cited by examiner

METHOD AND DEVICE FOR PRODUCING CURVED CUTS IN A TRANSPARENT MATERIAL

CROSS-REFERENCE TO RELATED APPLICATIONS

This application is a continuation of application Ser. No. 10/566,009 filed Jan. 25, 2006, entitled "Method and Device for Producing Curved Cuts in a Transparent Material" which is a national stage entry of PCT/EP04/08279 filed Jul. 23, 2004, which claims priority to DE 103 34 110.2 filed Jul. 25, 2003, each of which is hereby fully incorporated herein by reference.

TECHNICAL FIELD

The invention relates to a method of producing curved cuts in a transparent material, in particular in the cornea, by generating optical breakthroughs in the material by means of laser radiation focused into the material, wherein the focal point is three-dimensionally shifted in order to produce the cut by a series of optical breakthroughs, and wherein the shifting of the focal point is effected at a maximum speed which is lower in a first spatial direction than in the other two spatial directions. The invention further relates to an apparatus for producing curved cuts in a transparent material, in particular in the cornea, said apparatus comprising a laser radiation source which focuses laser radiation into the material and causes optical breakthroughs there, wherein a scanning unit which three-dimensionally shifts the focal point and a control unit which controls the scanning unit are provided, in order to produce the cut by sequential arrangement of the optical breakthroughs in the material, and wherein the scanning unit comprises adjustable optics for shifting the focal point in one spatial direction.

BACKGROUND

Curved cuts within a transparent material are generated, in particular, in laser-surgical methods, especially in ophthalmic surgery. This involves focusing treatment laser radiation within the tissue, i.e. beneath the tissue surface, so as to form optical breakthroughs in the tissue. In the tissue, several processes initiated by the laser radiation occur in a time sequence. If the power density of the radiation exceeds a threshold value, an optical breakthrough will result, generating a plasma bubble in the material. After the optical breakthrough has formed, said plasma bubble grows due to expanding gases. If the optical breakthrough is not maintained, the gas generated in the plasma bubble is absorbed by the surrounding material, and the bubble disappears again. However, this process takes very much longer than the forming of the bubble itself. If a plasma is generated at a material boundary, which may quite well be located within a material structure as well, material will be removed from said boundary. This is then referred to as photo ablation. In connection with a plasma bubble which separates material layers that were previously connected, one usually speaks of photo disruption. For the sake of simplicity, all such processes are summarized here by the term optical breakthrough, i.e. said term includes not only the actual optical breakthrough, but also the effects resulting therefrom in the material.

For a high accuracy of a laser surgery method, it is indispensable to guarantee high localization of the effect of the laser beams and to avoid collateral damage to adjacent tissue as far as possible. It is, therefore, common in the prior art to apply the laser radiation in a pulsed form, so that the threshold value for the power density of the laser radiation required to cause an optical breakthrough is exceeded only during the individual pulses. In this regard, U.S. Pat. No. 5,984,916 clearly shows that the spatial extension of the optical breakthrough (in this case, of the generated interaction) strongly depends on the pulse duration. Therefore, precise focusing of the laser beam in combination with very short pulses allows placement of the optical breakthrough in a material with great accuracy.

The use of pulsed laser radiation has recently become established practice particularly for laser-surgical correction of visual deficiencies in ophthalmology. Visual deficiencies of the eye often result from the fact that the refractive properties of the cornea and of the lens do not cause optimal focusing on the retina.

U.S. Pat. No. 5,984,916 mentioned above as well as U.S. Pat. No. 6,110,166 describe methods of the above-mentioned type for producing cuts by means of suitable generation of optical breakthroughs, so that, ultimately, the refractive properties of the cornea are selectively influenced. A multitude of optical breakthroughs are joined such that a lens-shaped partial volume is isolated within the cornea. The lens-shaped partial volume which is separated from the remaining corneal tissue is then removed from the cornea through a laterally opening cut. The shape of the partial volume is selected such that, after removal, the shape and the refractive properties of the cornea are thus modified so as to have the desired correction of the visual deficiency. The cuts required here are curved, which makes a three-dimensional adjustment of the focus necessary. Therefore, a two-dimensional deflection of the laser radiation is combined with simultaneous adjustment of the focus in a third spatial dimension.

The two-dimensional deflection of the laser radiation and the focus adjustment are both important for the accuracy with which the cut can be produced. At the same time, the speed of adjustment, which is achievable thereby, has an effect on the speed at which the required cut can be produced. Generating the cuts quickly is desirable not only for convenience or in order to save time; bearing in mind that movements of the eye inevitably occur during opthalmological operations, quick generation of cuts additionally contributes to the optical quality of the result thus achieved and avoids the requirement to track eye movements.

SUMMARY

Therefore, the invention improves a method and an apparatus of the above-mentioned type such that the time required to generate a cut is as short as possible.

According to the invention, this is achieved by a method of the aforementioned type, wherein the focal point is guided such that, with respect to the other two spatial directions, it follows contour lines of the cut which are located in planes that are substantially parallel to the first spatial direction.

This is further achieved by an apparatus of the above-mentioned type, wherein the control unit controls the scanning unit such that the focal point is guided in the remaining two spatial directions on contour lines of the cut which are located in planes perpendicular to the first spatial direction.

Thus, according to the invention, to generate the optical breakthroughs, paths are used which are based on contour lines of the cut to be produced. Said contour lines refer to that spatial direction of the system in which the slowest shifting speed is given. This allows maintenance of the focus almost unchanged in this spatial direction over a longer period, and the higher shifting speed in the other two spatial directions can be utilized without limitation. As a result, quick production of a cut is obtained. The contour lines can be conveniently obtained by cutting the curved cut in a plane perpendicular to the first spatial direction. The more exactly the planes of the contour lines are perpendicular to the first spatial direction, the more constant the shifting in the first spatial direction can be kept during one contour line.

For this purpose, the laser radiation is shifted relative to the two spatial directions which are perpendicular to the plane of the contour line, obeying the course of the contour line. It is possible, on the one hand, that the focal point exactly follows the respective contour line within certain tolerances. In this case, the focal point will describe concentrically located closed path lines, the focus being differently adjusted in the first spatial direction accordingly for each path line. Instead of closed path lines which exactly follow the contour lines within certain tolerances, it is also possible to connect the contour lines with each other in a contiguous manner. In doing so, the focal point is moved along a contour line, with individual contour lines not being formed as closed path lines, but adjacent contour lines being connected to each other by a smooth transition, so that, on the whole, the focal point is moved on a single contiguous path line. This generates a series of optical breakthroughs located on a closed path line, which form the cut surface. This uninterrupted sequential arrangement of contour lines may preferably be achieved by moving the focal point almost fully along the contour line, except for a respective residual portion, and causing a transition to the next contour line in said residual portion by then shifting the focal point in the first spatial direction. This approach has the advantage that the demands made on shifting in the first spatial direction are further reduced, because optical breakthroughs for producing the cut are also generated during said transition between two contour lines.

The contour line set will depend on the topography, i.e. the curvature of the cut. For a spherically curved cut, concentric circular contour lines are obtained. Since in ophthalmic corrections some astigmatism has to be corrected in most cases as well, a spherically curved cut will be rather an exception, whereas an ellipsoid or toroidal surface will be generally present. For such an ellipsoid surface, the contour lines are formed as (favorably concentric) ellipses. Ellipticity is preferably between 1.0 and 1.1, or even 1.2.

In the case of such a shape, the contour lines may also be used for guiding the focal point such that the deflected focal point follows an ellipsoid spiral, i.e. a spiral located on the peripheral surface of the curved cut.

The ellipticity of the ellipses or of the ellipsoid spiral, respectively, may depend on the shape of the corneal surface. Ellipticity is understood to be the ratio of the major axis of an ellipse to its minor axis.

For non-contacting methods, the natural surface topography is used; if a contact glass is used, the shape of such contact glass will play a role. The approach using a contact glass is advantageous here, because the topography is well-defined when a contact glass is attached by pressure. A planar contact glass represents a mathematical border-line case, and the concept of the contour line scan leads to the degeneracy of the path lines here, although they can also still be referred to as being closed. The case of a curved contact glass, which is more interesting also in terms of application, results in dependence of the surface topography, e.g. the ellipticity, on the curvature of the contact glass. This also applies if the curvature is purely spherical, because this will then also result in an ellipsoid shape of the cut surface. In most cases, however, ellipticity is not constant over the entire processing field, but often shows a radial dependence.

In principle, the following holds for the ellipticity e:

$$e(z) = \frac{\sqrt{R_a^2 - (R_a - z)^2}}{\sqrt{R_b^2 - (R_b - z)^2}},$$

wherein $R_a$ and $R_b$ designate the radiuses of curvature of the corneal surface in the direction of the major axes of the ellipse and z is the distance of the processing point (of the contour line) from the corneal vertex. Since z is then a function of the radial parameter of the processing field (distance from the optical axis), it is convenient to select $e(z)=e(z(r))$ for the already mentioned radial dependence of the ellipticity.

The above equation primarily holds for the non-contacted eye, because here, too, as mentioned above, an ellipsoid shape is present in most cases. Pressing against a contact glass usually results in a deformation which is considered in the calculation. In addition to spherical coordinates R, φ, α in the natural eye system and in the contact glass system (apostrophized coordinates) the outer radius of curvature of the cornea $R_{Cv}$ and the radius of curvature of the contact glass $R_G$ play a role. A simple and compact form of the transformation equations for this contact pressure transformation is:

φ'=φ

α'·R'=α·R $R_G-R'=R_{Cv}-R$

Further modifications leading to correction terms in the equations are possible, of course, and sometimes also useful. However, the heuristic approach disclosed here is only modified thereby and, thus, continues to apply in principle. The aforementioned relations enable easy calculation of the path lines, which also includes the calculation of ellipticity. A particularly important step in the algorithms for calculation is the above-indicated forward and backward transformation between the natural eye system and the contact glass system.

For a contact glass having a radius of curvature which corresponds approximately to that of the human eye, the ellipticity of the path lines is usually less than 1.4 (the great major axis being 10% longer than the small major axis). In the case of a sphero-cylindrical correction with −2 dpt and 1 dpt, ellipticity is, for example, only approximately 1.03 in the central field region near the optical axis and increases as the distance from the optical axis increases up to the outer path curve by approximately 10%. For a practicable embodiment, the variability of ellipticity or of a corresponding modification of an ideal circle path does not play an interfering role in the correction of visual defects and may, therefore, be assumed to be constant in a first approximation.

The distances between the contour lines to be used for control are naturally given by the distances of the planes which generate the contour lines by a mathematical section with the curved cut surface. In order to ensure that the multiplicity of optical breakthroughs forms a contiguous cut surface, care should be taken that the maximum distance of the contour lines does not exceed a limit value. For convenience, it is therefore preferred that distances of the contour lines in the first spatial direction be selected such that the distances between adjacent contour lines do not exceed a limit value. The measure to be used for this purpose may be either the distance in the contour line projection image or the distance in three-dimensional space. Since in ophthalmic surgery the curved cuts for optical correction in often sufficient approximation follow a spherical geometry or an ellipsoid geometry, respectively, within certain limits, it may suffice, for simplification, that the distances in the first spatial direction be selected such that the average distances of the contour lines are constant and, in particular, below a threshold value which is, of course, lower than the aforementioned limit value. For ellipsoid-shaped cut surfaces, the distance of adjacent contour lines can be simply evaluated in the contour line image at the long half-axes, in order to ensure that the arrangement of the optical breakthroughs is sufficiently tight.

In ophthalmologic operations, it may sometimes become necessary to also correct higher aberrations by removing volume from the cornea. The cut surface required for this purpose then accordingly also comprises higher orders of curvature. If it is desired to image these shapes directly via contour lines, this will sometimes result in a very complex contour line projection image, which requires complex and quick shifting in the other two spatial directions when tracking a contour line. For such cases, it is convenient to neglect the higher orders of curvature of the curved cut surface in determining the contour lines and then, while shifting the focal point in the other two spatial directions according to the contour line, to modify the shift in the first spatial direction according to the influence of the higher orders of curvature. Thus, the correction of higher aberrations is then modulated, in the first direction, e.g. in the z-direction, onto a basic movement which corresponds to the curved cut surface without higher aberrations.

Due to physiological conditions, it is advantageous, in many ophthalmic corrections for correction of visual defects, to remove a volume which is located in a circle-bordered region relative to the optical axis of the eye. In such cases, it is advantageous to sense an ellipse by means of the contour lines, while controlling the laser radiation (e.g. by an optical switch or stop or by manipulating the laser radiation source) in those peripheral regions in which the ellipse extends beyond the desired circular region, so that no optical breakthroughs are caused there. By blocking out peripheral regions of the ellipse in this manner, it can be ensured that the (astigmatically) curved cut surface is generated only in a circular region.

In the apparatus according to the invention, shifting of the focal point can be effected by a scanning unit, which comprises a zoom objective, preferably designed as an adjustable telescope, for shifting in the first spatial direction (usually the z-direction), and two tilting mirrors with crossed axes of rotation for the other two spatial directions (usually the x- and y-directions).

It is advantageous for the production of curved cuts caused by optical means, if the surface of the material, in particular the front surface of the cornea, has a defined shape. Further, it is convenient to spatially fix the material to be worked on, in particular the cornea, because sometimes complex beam re-adjustments can thus be dispensed with. It is convenient, under both aspects, to place onto the material a contact glass giving the material surface a particular shape. This shape is then considered when determining the contour lines. This may be effected, in particular, in that the above-mentioned coordinate transformation, which is effected by pressing against the contact glass, is input to the control.

In the apparatus, the shape given the surface of the material by the contact glass is known in the control unit or is suitably input to the latter, so that the control unit uses the surface shape of the material to select the contour lines.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
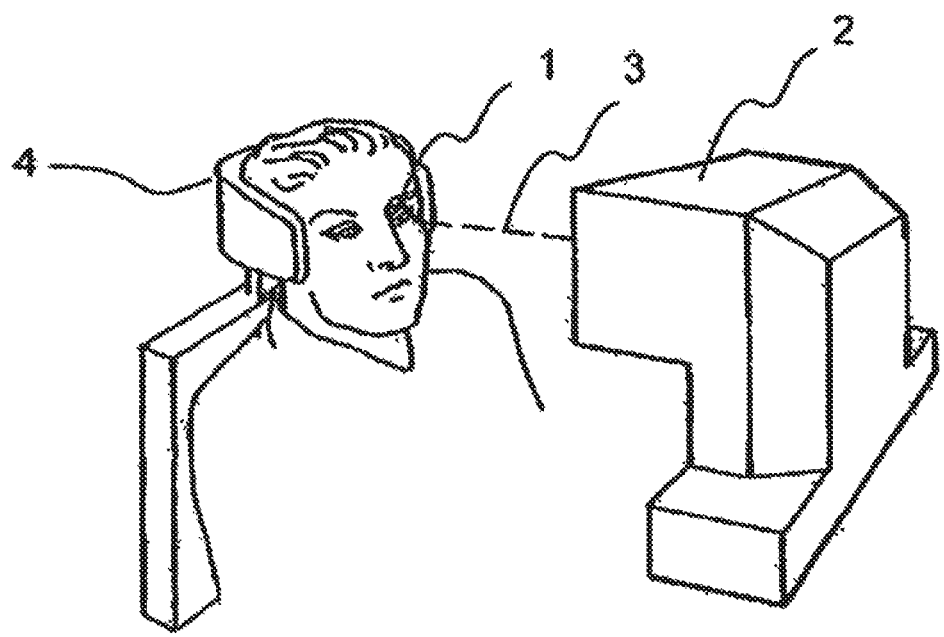
FIG. 1 is a perspective view of a patient during a laser-surgical treatment with a laser-surgical instrument.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 depicts a laser-surgical instrument for treatment of an eye 1 of a patient, said laser-surgical instrument 2 serving to effect a refractive correction. For this purpose, the instrument 2 emits a treatment laser beam 3 onto the eye of the patient 1 whose head is immobilized in a head holder 4. The laser-surgical instrument 2 is capable of generating a pulsed laser beam 3 allowing the method described in U.S. Pat. No. 6,110,166 to be carried out.

Figure 2:
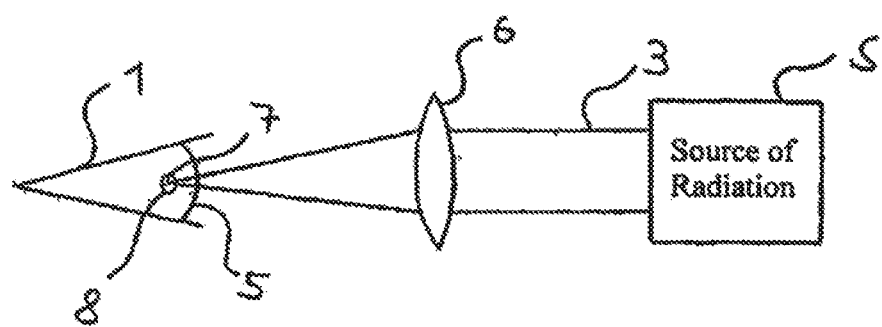
FIG. 2 depicts the focusing of a ray bundle onto the eye of the patient in the instrument of FIG. 1.

For this purpose, as schematically shown in FIG. 2, the laser-surgical instrument 2 comprises a source of radiation S whose radiation is focused into the cornea 5 1. A visual deficiency in the eye 1 of the patient is remedied using the laser-surgical instrument 2 to remove material from the cornea 5 so as to change the refractive characteristics of the cornea by a desired amount. In doing so, the material is removed from the corneal stroma, which is located beneath the epithelium and Bowman's membrane and above Descemet's membrane and the endothelium.

Material removal is effected in that layers of tissue in the cornea are separated by focusing the high-energy pulsed laser beam 3 by means of an objective telescope 6 in a focus 7 located within the cornea 5. Each pulse of the pulsed laser radiation 3 generates an optical breakthrough in the tissue, said breakthrough initiating a plasma bubble 8. As a result, the tissue layer separation covers a larger area than the focus 7 of the laser radiation 3. By suitable deflection of the laser beam 3, many plasma bubbles 8 are now arranged in series during treatment. The serially arranged plasma bubbles 8 then form a cut 9, which circumscribes a partial volume T of the stroma, namely the material to be removed from the cornea 5.

Due to the laser radiation 3, the laser-surgical instrument 2 operates in the manner of a surgical knife which, without injuring the surface of the cornea 5, separates material layers within the cornea 5. If the cut is led up to the surface of the cornea 5 by generating further plasma bubbles 8, material of the cornea 5 isolated by the cut 9 can be pulled out laterally and, thus, removed or extracted.

Figure 3:
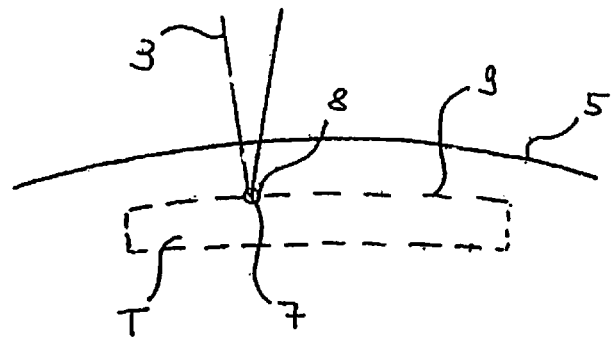
FIG. 3 is a schematic representation explaining a cut generated during laser-surgical treatment with the instrument of FIG. 1.

The generation of the cut 9 by means of the laser-surgical instrument 2 is schematically shown in FIG. 3. The cut 9 is formed by a series of plasma bubbles 8 produced as a result of continuous displacement of the focus 7 of the pulsed focused laser beam 3.

Figure 4:
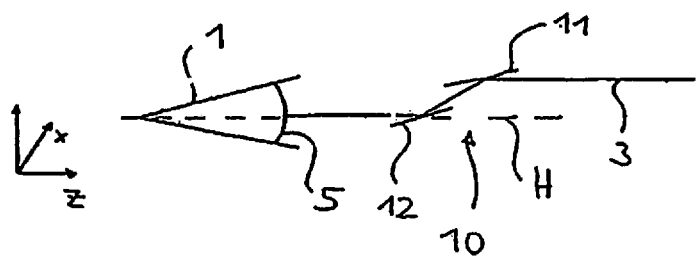
FIG. 4 depicts a deflection apparatus of the laser-surgical instrument of FIG. 1.

On the one hand, the focus shift according to one embodiment is effected by means of the deflecting unit 10, schematically shown in FIG. 4, which deflects the laser beam 3 along two mutually perpendicular axes, said laser beam 3 being incident on the eye 1 on a major axis of incidence H. For this purpose, the deflecting unit 10 uses a line mirror 11 as well as an image mirror 12, thus resulting in two spatial axes of deflection. The point where the main beam axis and the deflection axis cross is then the respective point of deflection. On the other hand, the telescope 6 is suitably adjusted for focus displacement. This allows shifting of the focus 7 along three orthogonal axes in the x/y/z coordinate system schematically shown in FIG. 4. The deflecting unit 10 shifts the focus in the x/y plane, with the line mirror allowing focus shift in the x-direction and the image mirror allowing adjustment of the focus in the y-direction. In contrast thereto, the telescope 6 acts on the z-coordinate of the focus 7.

If a cut as shown in FIG. 3 is curved in the same direction as the corneal surface, this can be achieved with an optical system whose image field curvature is similar to the curvature of the cornea, without the guide of the focus 7 having to take this into account.

Due to the corneal curvature, which is between 7 and 10 mm, the partial volume T is also curved accordingly. Thus, the corneal curvature is effective in the form of an image field curvature. This curvature is taken into account by suitable control of the deflecting unit.

Figure 5:
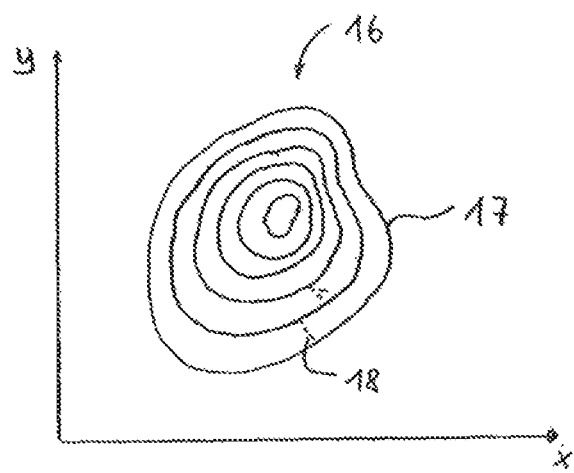
FIG. 5 depicts an exemplary contour line projection image, which is used to control the deflecting unit of FIG. 4.

In order to produce the cut 9, a contour line projection image 16 is determined from its curvature, such as that which is represented, by way of example, in the x/y plane in FIG. 5. The contour line image 16 consists of a multiplicity of concentric contour lines 17, which connect points having the same z-coordinates of the cut surface 9. The contour line projection image 16 was obtained by determining, e.g. filtering out, those points from the curved cut surface 9 which have at least approximately a certain z-coordinate. This corresponds to a mathematical section of the curved cut surface 9 with an x/y plane at the respective z-coordinate. In order to generate the individual contour lines 17 of the contour line image 16 of FIG. 5, the z-coordinates were selected such that the distances between adjacent contour lines 17 in the contour line image 16 do not exceed a predetermined limit value. This limit value is defined by the maximum admissible distance between two plasma bubbles 8 which is admissible in order to achieve a contiguous cut surface.

In order to produce the cut 9, the focus 7 is now shifted by the deflecting unit 10 according to the contour lines 17, while the zoom optics 6 adjust the corresponding z-coordinate of the focus 7 for each contour line 17. While the focus 7 passes over a contour line 17, the telescope 6 remains fixed, and is adjusted merely during the transitions 18 between adjacent contour lines, which transitions are shown in broken lines in FIG. 5.

Figure 6:
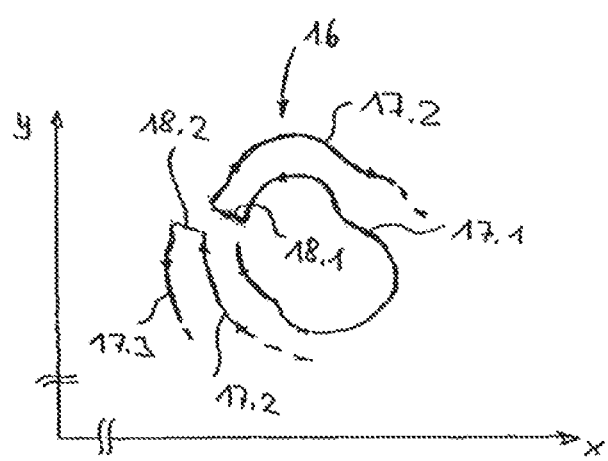
FIG. 6 depicts a detail of a contour line image similar to that of FIG. 5 in order to explain the transition between subsequent contour lines.

FIG. 6 shows a detail of the contour line image 16. Each contour line 17 is traced by the focus 7 as an almost completely closed curve, with the distance between the start and the end of a contour line 17 not exceeding the maximum distance between two plasma bubbles 8 which is defined by the limit value. At the end of each contour line 17 (in FIG. 6, three contour lines 17.1, 17.2 and 17.3 are indicated), a transition 18 is effected by adjusting the telescope 6 to the respective next contour line. Thus, there is a transition 18.1 between the contour lines 17.1 and 17.2, and a transition 18.2 between the contour lines 17.2 and 17.3. This continues for all contour lines. By the transition thus selected it is achieved, on the one hand, that the limit value for the maximum admissible distance between two plasma bubbles 8 is not exceeded and, on the other hand, the contour lines 17 can be written as a contiguous track.

Figure 7:
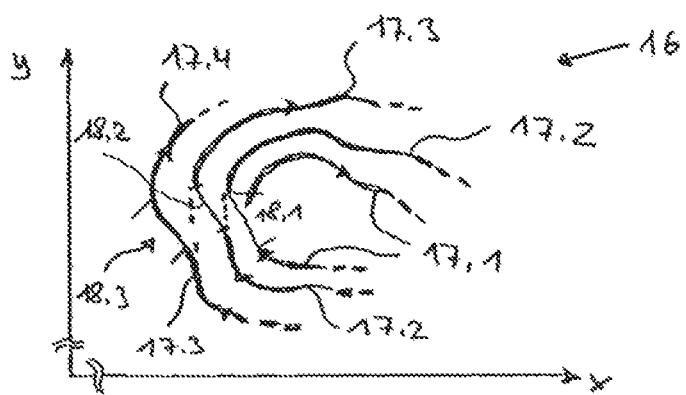
FIG. 7 is similar to FIG. 6, with a further possible transition between contour lines.

In FIG. 6, the transitions 18 are located substantially on lines of steepest descent of the curved cut surface 9. In this regard, FIG. 7 shows different transitions 18.1 to 18.3, where a smooth transition is effected between the end of one contour line and the start of the immediately adjacent contour line. For clarification, the continuation of the corresponding contour lines is shown in broken lines in FIG. 7, which continuation is not tracked by the focus 7. As can be seen, a smooth transition to the next contour line is effected at the end of a contour line 17 by suitable control of the line mirror 11 as well as of the image mirror 12. At the same time, the telescope 6 is simultaneously adjusted during the transitions 18.1, 18.2 and 18.3 thus achieved.

In contrast to the transition of FIG. 6 in which the adjacent contour lines are traced in the opposite direction of rotation, this results in a unidirectional rotation about the contour lines, which are serially arranged in a manner similar to a spiral. However, unlike a real spiral, the contour line is traced by the focus 7 except for the transition 18, and the change from one contour line to the next is effected over a small angular range of the rotation, instead of continuously in a 360° rotation.

Figure 8A:
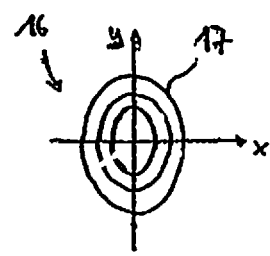
FIGS. 8a and 8b depict a further example of a contour line image, including associated control functions for the deflecting unit of FIG. 4.
Figure 8B:
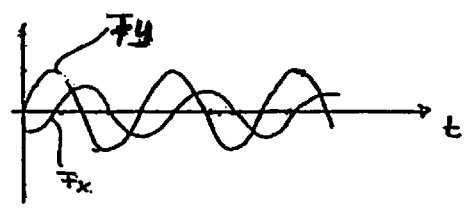

FIG. 8a shows a further example of a contour line image 16, which is composed of concentric elliptical contour lines 17 here. For this contour line image, the temporal control of the line mirror 11 and the image mirror 12 is provided as schematically represented for each contour line 17 in FIG. 8b, wherein the mirrors are controlled by control functions Fy and Fx that satisfy the equation $\sin \varphi$ or $A \cdot \sin(\varphi + \alpha)$ and $\cos \varphi$ or $R \cdot \cos(\varphi + \alpha)$ ($\varphi$ being the angular parameter of the contour line, $\alpha$ being the parameter R of the angular position acting on the major axis of the ellipse relative to the y-axis, and A being the parameter influencing ellipticity, wherein R=1 holds true in most cases).

Figure 9:
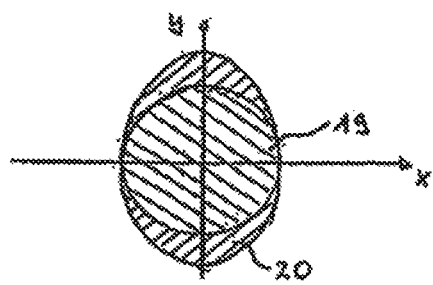
FIG. 9 is a top view of a cut region as an ophthalmic operation for correction of a visual defect is being carried out.

Since for a non-circular contour line projection image the cut surface 9 viewed in the z-direction would comprise a non-circular region, which is not desirable in ophthalmologic terms, in one embodiment, the radiation source S is controlled such that no optical breakthrough, i.e. no plasma bubble 8, is generated in the material 5 in regions located outside a circular region of such rotationally non-symmetrical contour line images. This is shown in FIG. 9 by differently shaded areas. In the circular region 19, which is shaded from upper left to lower right, the radiation source S can generate plasma bubbles 8. In the regions 20 protruding beyond, in which the contour line image 16 exceeds the desired circular region 19, however, the radiation source S is inoperative or is at least operated such that no plasma bubbles 8 can be generated.

Figure 10:
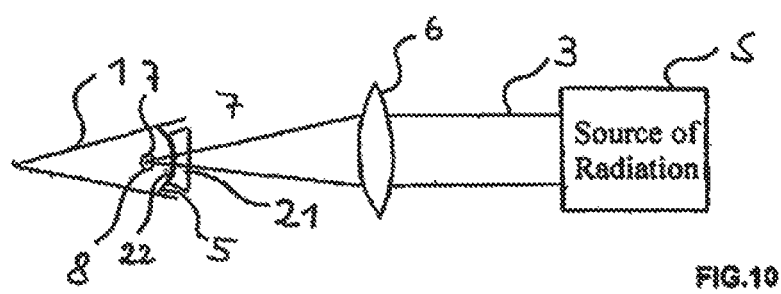
FIG. 10 is a representation similar to that of FIG. 2, using a contact glass.

The laser-surgical instrument 2 as well as the method carried out thereby have been described so far in connection with a concept which leaves the shape of the front surface of the cornea unchanged during the operation. However, the above description also applies to approaches of placing a contact glass on the cornea 5. The structure present in such an approach is shown schematically in FIG. 10, which substantially corresponds to FIG. 2, so that no further details are given for elements already described in connection with FIG. 2. However, in contrast to FIG. 2, the cornea 5 now has a contact glass 21 fitted thereon, the inner surface 22 of which imparts a certain profile to the front surface of the cornea 5. In contrast to the previously described approach, in determining the path lines, e.g. of the contour lines, not the curvature of the cornea 5 in the free, i.e. natural, condition is to be considered, but the shape given by the interior surface 22 of the contact glass 21.

Figure 11:
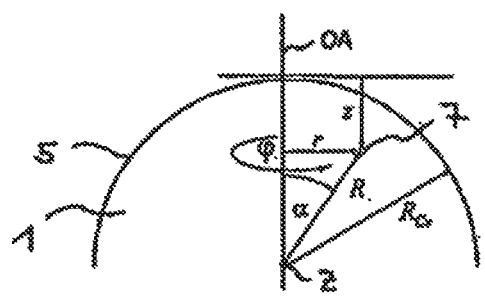
FIG. 11 depicts parameters relevant to determining the contour lines.

Without the contact glass 21, the geometrical conditions of the eye 1 are as shown in FIG. 11. Relative to the center Z of the eye, the cornea 5 is approximately spherically curved, so that its position is unambiguously determined by the radius of curvature $R_{Cv}$ and the position of the center Z on the optical axis OA. The coordinates of a point at which a laser focus 7 impinges in order to generate a plasma bubble 8 can thus be unambiguously indicated either in cylinder coordinates (radius r from the optical axis OA, distance z from the vertex plane and angle $\varphi$) or in spherical coordinates (radius r from the center Z of the eye, angle $\varphi$ and $\alpha$). In both coordinate systems, the contour lines or the path lines, respectively, along which the focus 7 is shifted, can be calculated and indicated, elliptical path lines being particularly easily described mathematically in cylinder coordinates.

Figures 12, 13:
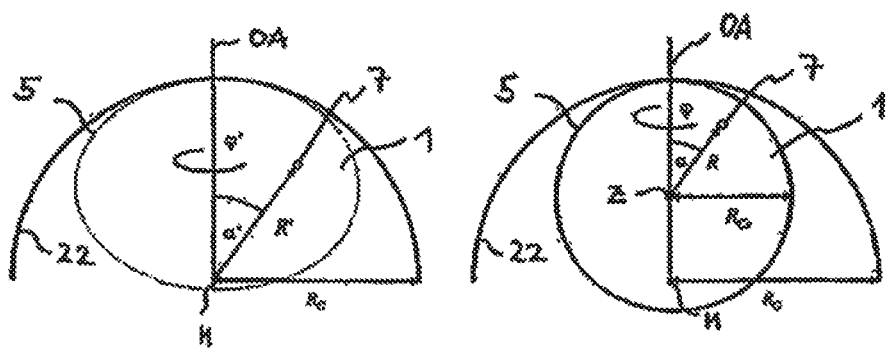
FIGS. 12 and 13 depict the parameters of FIG. 11 with and without a contact glass.

If a contact glass 21 is placed on the eye, then the conditions shown in FIG. 13 are present as long as the interior surface 22 of the contact glass 21 does not deform the cornea. The contact glass is spherically curved here, with the radius of curvature $R_G$ being greater than the radius of curvature $R_{Cv}$ of the cornea. If the contact glass 21 is pressed on the eye 1 now, the cornea 5 deforms from a sphere to an ellipsoid; the conditions schematically shown in FIG. 12 arise. Thus, the contact pressure causes a deformation of the eye, which then contacts the interior surface 22 of the contact glass 21 considerably more closely than without said contact pressure, at least in a region around the optical axis OA.

Since the geometrical conditions change now, the pressing operation can be understood, with respect to the mathematical description of the locations of the focal points 7, and thus of the path lines, as a coordinate transformation, which is also referred to as "contact pressure transformation". The transformed coordinates are then conveniently related to the center M of the preferably spherically curved contact glass, because the contact glass is usually also used for fixation of the eye 1, i. e. the eye is permanently connected to the instrument 2. The double function of the contact glass (imparting of a shape and spatial fixation) is effective here.

One obtains elliptical path lines. The ellipticity of the path lines depends on the shape of said contact glass. Ellipticity is understood to be the ratio of the great major axis of an ellipse to its small major axis.

A planar contact glass represents a mathematical borderline case, and the concept of the contour line scan leads to the degeneracy of the path lines here, although they can also still be referred to as being closed. The case of a curved contact glass, which is more relevant also in terms of application, results in the ellipticity being dependent on the curvature of the contact glass. Moreover, in most cases, ellipticity is not constant over entire processing field, but shows a radial dependence.

In principle, the following holds for the ellipticity e:

$$e(z) = \frac{\sqrt{R_a^2 - (R_a - z)^2}}{\sqrt{R_b^2 - (R_b - z)^2}},$$

wherein $R_a$ and $R_b$ designate the radiuses of curvature of the corneal surface in the direction of the major axes of the ellipse and z is the distance of the processing point (of the contour line) from the corneal vertex. Since z, in the selected cylinder coordinate system (z, distance from the corneal vertex; r, distance from the optical axis; $\varphi$), is then a function of the radial parameter v of the processing field, it is convenient to describe the radial dependence of the ellipticity by $e(z)=e(z(r))$.

The above-mentioned equation primarily holds true for the non-contacted eye. Pressing against a contact glass usually results in a deformation which has to be considered in the calculation. The outer radius of curvature of the cornea $R_{Cv}$ and the radius of curvature of the contact glass $R_G$ play a role then. A simple and compact form of the transformation is:

$\varphi'=\varphi$ $\alpha'\cdot R'=\alpha\cdot R$ $R_G-R'=R_{Cv}-R$

Further modifications leading to correction terms in the equations are possible, of course, and sometimes also useful. However, the above approach is only modified there and, thus, still applies, in principle. The aforementioned relations enable calculation of the path lines, which also includes the calculation of ellipticity. A particularly important step in the algorithms for calculation is the forward and backward transformation between the natural eye system and the contact glass system.

For a contact glass having a radius of curvature which corresponds approximately to that of the human eye, the ellipticity of the path lines is usually less than 1.2 (great major axis 10% longer than the small major axis). In the case of a sphero-cylindrical correction with −2 dpt and 1 dpt, the ellipticity is, for example, only approximately 1.03 in the central field region near the optical axis and increases as the distance from the optical axis increases up to the outer path curve by approximately 10%. For an embodiment, the variability of ellipticity or of a corresponding modification of an ideal circle path does not play an interfering role in the higher-order correction of visual defects, and may, therefore, be assumed to be constant in a first approximation.

It is emphasized once again that the use of contour lines according to the invention is applicable to approaches both with and without a (planar or curved) contact glass; however, the use of a contact glass obviates any need for tracking and there is no uncertainty with respect to the existing surface topography.

If a contact glass is used, the surface topography can be determined by suitable methods and apparatuses and is then also considered (analogously) in the method just like the topography defined by the pressing operation.

If the shape of the contact glass surface can not be described by a sphere, but follows a different spatial area function, for example a paraboloid, a law of transformation can be given in analogy to the above-indicated transformation, said law following the same physical concept, however.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of producing a three dimensional curved cut in an interior of transparent material of an eye, the method comprising:
    defining a 3D shape of the curved cut relating to a natural topography of a front face of the eye;
    immobilizing the eye by pressing a contact glass onto the front face of the eye, wherein the contact glass deforms the front face of the eye;
    determining a change in topography of the front face caused by the contact glass deforming of the front face;
    defining 3D focus positions on basis of the 3D shape of the curved cut related to the natural topography of the front face of the eye and the change in topography between the natural topography of the front face of the eye and the topography of the front face of the eye as deformed by the contact glass;
    focusing laser radiation to a focus point in the interior of the material;
    3D shifting the focus point over the focus positions;
    generating optical breakthroughs in the material during the 3D shifting to produce the three dimensional curved cut from a series of optical breakthroughs.

2. The method according to claim 1, further comprising selecting the transparent material to be a cornea of the eye.

3. The method according to claim 1, further comprising selecting the 3D shape of the curved cut relating to the natural topography to be spherical ellipsoidal or toroidal.

4. The method according to claim 1, further comprising making the series of optical breakthroughs follow a spiral, at least in sections of the cut.

5. The method according to claim 4, further comprising making distances between adjacent path lines of the spiral substantially constant.

6. The method according to claim 4, further comprising making distances between adjacent path lines of the spiral constant within a tolerance of plus or minus about ten percent.

7. The method according to claim 1, further comprising selecting the contact glass to comprise a spherical contact surface which is pressed onto the front face of the eye.

8. The method according to claim 1, further comprising selecting the contact glass to comprise a contact surface of known shape which is pressed onto the front face of the eye and wherein determining the change in topography of the front face caused by the contact glass deforming of the front face comprises taking known shape of the contact surface as shape of the front face deformed by the contact glass.

9. The method according to claim 8, wherein determining the change in topography of the front face caused by the contact glass deforming of the front face further comprises determining a transformation of coordinates relating to the natural and un-deformed front face of the eye into coordinates relating to the front face deformed by the contact glass.

10. The method according to claim 9, further comprising selecting the contact surface to be spherical and describing the transformation by $\varphi'=\varphi$, $\alpha'\cdot R'=\alpha\cdot R$, and $R_G-R'=R_{Cv}-R$, wherein $R$, $\varphi$, $\alpha$ are spherical coordinates relating to the natural and un-deformed front face of the eye, $R'$, $\varphi'$, $\alpha'$ are spherical coordinates relating to the contact surface, $R_{Cv}$ is a radius of curvature of the cornea, and $R_G$ is a radius of curvature of the spherical contact surface.

11. The method according to claim 1, further comprising:
defining a desired correction of visual deficiencies of the eye, and
determining a volume to be removed from the eye required to obtain the desired correction,
wherein defining the 3D shape of the curved cut comprises defining the cut such that it circumscribe the volume and prepares the volume for extraction from the eye.

12. The method according to claim 11, further comprising determining the volume to be located fully below the front face of the eye.

13. The method according to claim 12, further comprising extracting of the volume thereby changing a curvature of the front face of the eye.

14. A method of eye treatment comprising producing a three-dimensional curved cut in an interior of transparent material of an eye, the method comprising:
defining a 3D shape of the curved cut relating to a natural topography of a front face of the eye;
immobilizing the eye by pressing a contact glass onto the front face of the eye, wherein the contact glass deforms the front face of the eye;
determining a change in topography of the front face caused by the contact glass deforming of the front face;
defining 3D focus positions on basis of the 3D shape of the curved cut related to the natural topography of the front face of the eye and the change in topography between the natural topography of the front face of the eye and the topography of the front face of the eye as deformed by the contact glass;
focusing laser radiation to a focus point in the interior of the material;
3D shifting the focus point over the focus positions;
generating optical breakthroughs in the material during the 3D shifting to produce the 3D shaped cut from a series of optical breakthroughs,
wherein the cut circumscribes a volume which is located fully below the front face of the eye so that the volume that is circumscribed is removable from the eye, and
further comprising removing the volume from the eye by pulling the volume from the eye after the cut has been generated.

15. The method according to claim 14, further comprising selecting the transparent material to be a cornea of the eye.

16. The method according to claim 14, further comprising selecting the 3D shape of the curved cut relating to the natural topography to be spherical ellipsoidal or toroidal.

17. The method according to claim 14, further comprising making the series of optical breakthroughs to follow a spiral, at least in sections of the cut.

18. The method according to claim 17, comprising making distances between adjacent path lines of the spiral to be substantially constant.

19. The method according to claim 17, further comprising making distances between adjacent path lines of the spiral to be constant within a tolerance of plus or minus about ten percent.

20. The method according to claim 14, further comprising selecting the contact glass to comprise a spherical contact surface which is pressed onto the front face of the eye.

21. The method according to claim 14, further comprising selecting the contact glass to comprise a contact surface of known shape which is pressed onto the front face of the eye and wherein the step of determining the change in topography of the front face caused by the contact glass deforming of the front face comprises taking known shape of the contact surface as shape of the front face deformed by the contact glass.

22. The method according to claim 21, wherein determining the change in topography of the front face caused by the contact glass deforming of the front face further comprises determining a transformation of coordinates relating to the natural and un-deformed front face of the eye into coordinates relating to the front face deformed by the contact glass.

23. The method according to claim 22, further comprising selecting the contact surface to be spherical and describing the transformation by $\varphi'=\varphi$, $\alpha' \cdot R' = \alpha \cdot R$, and $R_G - R' = R_{Cv} - R$, wherein R, $\varphi$, $\alpha$ are spherical coordinates relating to the natural and un-deformed front face of the eye, R', $\varphi'$, $\alpha'$ are spherical coordinates relating to the contact surface, $R_{Cv}$ is a radius of curvature of the cornea, and $R_G$ is a radius of curvature of the spherical contact surface.

24. The method according to claim 14, further comprising:
defining a desired correction of visual deficiencies of the eye, and
determining a volume to be removed from the eye required to obtain the desired correction,
wherein the step of defining the 3D shape of the curved cut comprises defining the cut such that it circumscribe the volume and prepares the volume for extraction from the eye.

25. The method according to claim 24, further comprising describing the volume to be located fully below the front face of the eye.

26. The method according to claim 25, further comprising extracting the volume thereby changing a curvature of the front face of the eye.

* * * * *